United States Patent
Saito et al.

(10) Patent No.: US 6,858,428 B2
(45) Date of Patent: Feb. 22, 2005

(54) HUMAN AND ANIMAL CELL CULTURE MEDIUM CONTAINING ANTITHROMBIN III FOR SUPPRESSING CELL DEATH

(75) Inventors: Takao Saito, Aichi (JP); Sumio Maeda, Aichi (JP); Hidetoshi Inagaki, Aichi (JP)

(73) Assignee: Agency of Industrial Science and Technology, Tokyo (JP)

( * ) Notice: Subject to any disclaimer, the term of this patent is extended or adjusted under 35 U.S.C. 154(b) by 59 days.

(21) Appl. No.: 10/214,303

(22) Filed: Aug. 8, 2002

(65) Prior Publication Data

US 2002/0197719 A1 Dec. 26, 2002

Related U.S. Application Data

(62) Division of application No. 09/513,313, filed on Feb. 25, 2000, now abandoned.

(30) Foreign Application Priority Data

Jul. 19, 1999 (JP) ............................................ 11-204087

(51) Int. Cl.$^7$ .............................. C12N 5/00; C12N 5/02
(52) U.S. Cl. ...................................... 435/325; 435/404
(58) Field of Search .................................. 435/325, 404

(56) References Cited

U.S. PATENT DOCUMENTS

| | | | |
|---|---|---|---|
| 4,446,126 A | 5/1984 | Jordan | |
| 4,689,323 A | 8/1987 | Mitra et al. | |
| 4,900,720 A | 2/1990 | Kotitschke | |
| 5,114,847 A | 5/1992 | Jungfer et al. | |
| 5,316,911 A | 5/1994 | Baek et al. | |
| 5,989,593 A | 11/1999 | Ideno et al. | |
| 6,307,028 B1 | 10/2001 | Lebing et al. | |

*Primary Examiner*—David M. Naff
*Assistant Examiner*—Deborah K. Ware
(74) *Attorney, Agent, or Firm*—Oblon, Spivak, McClelland, Maier & Neustadt, P.C.

(57) ABSTRACT

The present invention provides low serum or serum free liquid culture media for human or animal cells, and the present invention relates to culture media containing antithrombin III and optionally heparin for the low-serum or serum-free culture of human or animal cells to suppress cell death. The antithrombin III is purified from human, bovine, or other animal serum, or antithrombin III derived from recombinant bacteria or cells containing the full length of the antithrombin III gene.

21 Claims, No Drawings

HUMAN AND ANIMAL CELL CULTURE MEDIUM CONTAINING ANTITHROMBIN III FOR SUPPRESSING CELL DEATH

CROSS-REFERENCE TO A RELATED APPLICATION

The present application is a Divisional application of U.S. Ser. No. 09/513,313, which was filed on Feb. 25, 2000 and is now abandoned.

BACKGROUND OF THE INVENTION

1. Field of the Invention

The present invention relates to culture media for low-serum or serum-free culture of human or animal cells, and in particular to novel human and/or animal cells culture media which effectively control cell death of cultured human or animal cells when used in the production of biological substances, in biological analysis, or the like.

2. Description of the Prior Art

When industrially useful biological substances such as plasma proteins and antibodies are produced using human and animal cells, or when human and animal cells are used for biological analysis, the serum that is usually added in a concentration of 5 to 10% to the culture medium makes it extremely difficult to purify the product and to make an analysis thereof. Low-serum culture with the addition of minimal amounts of serum or serum-free culture have thus been proposed and developed. Various serum-free culture media have been developed for serum-free culture, most of which involve the addition of alternative substances for the effects of serum, such as transferrin, albumin and similar plasma proteins, steroid hormones, insulin and similar hormones and growth factors, amino acids, vitamins and similar nutrient factors, and the like. Recombinant human and animal cell lines containing a gene for controlling cell death have recently been designed, and there is ongoing research on the serum-free culture of human and animal cell lines which have been genetically engineered to prevent cell death normally induced under serum-free conditions.

Two types of cell death are induced during serum-free culture; cell death induced as a result of starvation due to a lack of nutrient factors, and cell death occurred as a result of apoptosis induced by a lack of specific proteins in serum. However, cell death arising as a result of the induction of apoptosis cannot be addressed with the nutrients conventionally added to serum-free culture, such as transferrin, albumin and similar plasma proteins, steroid hormones, insulin and similar hormones and growth factors, amino acids, vitamins and similar nutrient factors. There is thus a need to develop factors for controlling cell death, including apoptosis.

An object of the present invention is to provide a useful novel human and animal cells culture medium for controlling cell death, including apoptosis, which occurs during serum-free culture when industrially useful biological substances such as plasma proteins and antibodies are produced using human or animal cells or when human or animal cells are used for biological analysis.

As a result of extensive research, the inventors discovered that antithrombin III has considerable effect in controlling cell death, including apoptosis, which occurs during serum-free culture, and this invention has been accomplished according to this discoveries.

That is, the invention is intended to provide novel culture media for the serum-free culture of human or animal cells, containing purified and added antithrombin III from human, bovine, or other animal serum, or antithrombin III from recombinant bacteria or cells containing the full length of the antithrombin III gene.

SUMMARY OF THE INVENTION

The present invention is to provide human and animal cell culture media.

The present invention relates to culture media for low-serum or serum-free culture of human or animal cells, containing purified and added antithrombin III from human, bovine, or other animal serum, or antithrombin III derived from recombinant bacteria or cells containing the full length of the antithrombin III gene.

The present invention is highly effective in controlling cell death, including apoptosis, which occurs during the serum-free culture of human or animal cells.

The present invention for achieving the aforementioned objects comprises the following technical means.

(1) Human or animal cells culture medium having function suppressing cell death in human or animal cultured cells, comprising added antithrombin III component and other component of a culture medium.

(2) The human or animal cells culture medium according to (1) above, wherein the antithrombin III is antithrombin III from serum, or antithrombin III from recombinant bacteria or cells containing the full length of the antithrombin III gene.

The present invention is described in further detail below.

The present invention relates to culture media for the low-serum or serum-free culture of human or animal cells. With the exception of the antithrombin III, the other components of the medium are not particularly limited. The present invention includes any media, of any type, provided that the medium is for the culture of human and animal cells. Examples of media for the low-serum or serum-free culture of human and animal cells include serum-free media for fibroblasts, epidermal cells, and hybridomas, as well as many other media. The media of the present invention are applicable to any liquid medium for such low-serum or serum-free culture.

In the present invention, an antithrombin III component is added to the human or animal cells medium.

As used in the present invention, the added antithrombin III means adding antithrombin III itself as a specific component to the medium, and thus means the antithrombin III component itself thus added to the medium. Examples of the antithrombin III component include, but are not limited to, antithrombin III purified from human and animal serum. Any component having the same effect as the aforementioned antithrombin III can also be used. For example, antithrombin III derived from recombinant bacteria or cells containing the full length of the antithrombin III gene can similarly be used.

Antithrombin III in the form of commercially available lyophilized products can be used. Various conventional manufacturing methods therefor have been reported. A product can be produced in the following manner, for example.

Human or animal serum, or culture broth of recombinant bacteria or cells containing the antithrombin III gene, can be treated on an antibody column against antithrombin III to obtain antithrombin III-rich fractions. The fractions can be furthermore purified by filtration or using an ion exchange column so as to produce antithrombin III.

The antithrombin III can be used after having been previously added as part of a culture medium, or it can be used by subsequently being added to an existing culture medium. The concentration of antithrombin III is preferably between 25 and 50 $\mu$g/mL. Although the antithrombin III is usually added in a concentration of 1 $\mu$g/mL or more, its effects in controlling cell death can be enhanced with the concurrent use of heparin.

The antithrombin III added to the culture media in the present invention has been confirmed to be highly effective in controlling cell death in low concentrations, including the apoptosis of human and animal cells such as hepatoma cells and osteoblasts which occurs during serum-free culture, for example. The addition of antithrombin III has been confirmed to be highly effective in media for serum-free culture of human and animal cells, as well as for low-serum culture with a serum concentration of 5% or less.

BEST MODE FOR CARRYING OUT OF THE INVENTION

EXAMPLES

The present invention is described in detail below with reference to examples. Although the following examples are preferred embodiments of the present invention, the present invention is not in any way limited to these examples.

Example 1

In this example, we studied how the addition of antithrombin III affected hepatoma cell death during serum-free culture.
(1) Preparation of Antithrombin III
Lyophilized antithrombin III purified from bovine serum was used, and was cultured after being diluted with culture medium to the predetermined concentration.
(2) Culture of Hepatoma Cells
Two mL cell suspension of hepatoma cell line HepG2 dispersed in trypsin ($5 \times 10^5$ cells) were inoculated on six multi-well plates and pre-culture by using Dulbecco's modified Eagle medium (DMEM) containing 5% fetal bovine serum, 1.6 g/L sodium hydrogencarbonate, 0.584 g/L L-glutamine, and 0.08 g/L kanamycin sulfate at 37° C. in a 5% $CO_2$ gas phase. After one day, the broth was recovered, the cell surfaces were washed with serum-free medium, and the culture was continued for another 3 days with the addition of medium containing 5%, 0% fetal bovine serum, and 2 mL of fresh medium comprising the growth factors and hormones given in Table 1, which have been reported as survival factors, and antithrombin III, albumin, orosomucoid, transferrin, or typical serum proteins such as α1-antitrypsin, which were added to media containing no fetal bovine serum (0%). The viable cell count was assayed after 3 days of culture.
(3) Results The results are given in Table 1.

Although 90% or more of the cells had survived after 3 days of culture in the medium with a 5% serum concentration, the survival rate dropped considerably in the serum-free medium with a serum concentration of 0%. The addition of albumin, orosomucoid, holotransferrin, and α 1-antitrypsin to serum-free media resulted in virtually the same survival rate as that of the serum-free medium with a serum concentration of 0%, indicating virtually no effect in controlling cell death. The use of a serum-free medium containing antithrombin III, on the other hand, resulted in virtually the same survival rate as that of the medium with a 5% serum concentration.

TABLE 1

| Culture medium | Concentration of additives | Survival rate (%) |
|---|---|---|
| DMEM + Fetal bovine serum 5% | | 95.8 |
| DMEM | | 59.5 |
| + Antithrombin III | 17.5 μg/ml | 93.3 |
| + aFGF | 10 ng/ml | 59.6 |
| + bFGF | 10 ng/ml | 55.2 |
| + IGF-1 | 50 ng/ml | 45.3 |

TABLE 1-continued

| Culture medium | Concentration of additives | Survival rate (%) |
|---|---|---|
| + PDGF-AA | 50 ng/ml | 54.0 |
| + EGF | 50 ng/ml | 54.7 |
| + Insulin | 0.1 μM | 53.0 |
| + Albumin | 225 μg/ml | 65.0 |
| + Orosomucoide | 48.8 μg/ml | 61.5 |
| + Transferrin | 150 μg/ml | 62.8 |
| + α 1-antitrypsin | 150 μg/ml | 72.7 |

The results in Example 1 above show that the growth factor, hormones, and typical serum proteins which were used for comparison had virtually no effect in controlling cell death, including the apoptosis of hepatoma cells which occurs during serum-free culture, whereas the antithrombin III used in the present invention was considerably effective in controlling cell death.

Example 2

In this example, we studied how the concentration of antithrombin III affected hepatoma cell death during serum-free culture.

The hepatoma cell line HepG2 was pre-cultured in the same manner as in Example 1. After 1 day, the broth was recovered, the cell surfaces were washed with serum-free medium, and the culture was continued for another 3 days with the addition of medium containing 5%, 0% fetal bovine serum, or 2 mL of fresh medium comprising antithrombin III added in concentrations ranging from 1 to 25 μg/mL to media containing no fetal bovine serum (0%). The viable cell count was assayed after 3 days of culture. The results are given in Table 2.

TABLE 2

| Culture medium | Concentration of additives (μg/ml) | Survival rate (%) |
|---|---|---|
| DMEM + Fetal bovine serum 5% | | 92.6 |
| DMEM | | 63.3 |
| + Antithrombin III | 1 | 68.6 |
| | 2.5 | 68.0 |
| | 5 | 74.1 |
| | 10 | 88.5 |
| | 25 | 94.0 |

The results in Table 2 show that cell death was suppressed in serum-free media containing antithrombin III in a concentration of 1 μg/mL, and that a concentration of 2.5 μg/mL resulted in virtually the same survival rate as a serum concentration of 5%, demonstrating that the antithrombin III used in the present invention was extremely effective at low concentrations of 1 to 2.5 μg/mL in controlling cell death, including the apoptosis of hepatoma cells occurring during serum-free culture.

Example 3

In this example, we studied how the addition of antithrombin III affected osteoblast cell death during serum-free culture.

Two mL cell suspension of osteoblast cell line ROS dispersed in trypsin ($5 \times 10^5$ cells) were inoculated on six multi-well plates and pre-cultured by using Dulbecco's modified Eagle medium (DMEM) containing 10% fetal bovine serum, 1.6 g/L sodium hydrogencarbonate, 0.584 g/L L-glutamine, and 0.08 g/L kanamycin sulfate at 37° C. in a 5% $CO_2$ gas phase. After one day, the broth was recovered, the cell surfaces were washed with serum-free medium, and the culture was continued for another 3 days with the addition of medium containing 10%, 0% fetal bovine serum, or 2 mL of fresh medium comprising 13 μg/mL antithrombin III added to media containing no fetal bovine serum (0%). The viable cell count was assayed after 3 days of culture. The results are given in Table 3.

TABLE 3

| Culture medium | Concentration of additives (μg/ml) | Survival rate (%) |
| --- | --- | --- |
| DMEM + Fetal bovine serum 5% | | 96.8 |
| DMEM | | 70.2 |
| + Antithrombin III | 13 | 85.5 |

The results in Table 3 show that virtually 100% of the cells had survived after 3 days of culture at a serum concentration of 10%, but that the survival rate dropped considerably in serum-free culture. However, the use of serum-free medium containing antithrombin III in a concentration of 13 μg/mL was considerably effective in controlling cell death. The effect of antithrombin III in controlling cell death, including apoptosis, was thus not limited to the hepatoma cell line HepG2, but was also found to be effective for other cells.

Example 4

In this example, we studied the effects of protease inhibitors on hepatoma cell death during serum-free culture.

The hepatoma cell line HepG2 was pre-cultured in the same manner as in Example 1. After 1 day, the broth was recovered, the cell surfaces were washed with serum-free medium, and the culture was continued for another 3 days with the addition of medium containing 5%, 0% fetal bovine serum, or 2 mL of fresh medium comprising antithrombin III or any of various synthetic protease inhibitors given in Table 4 added to media containing no fetal bovine serum (0%). The viable cell count was assayed after 3 days of culture. The results are given in Table 4.

TABLE 4

| Culture medium | Concentration of additives (μg/ml) | Survival rate (%) |
| --- | --- | --- |
| DMEM + Fetal bovine serum 5% | | 97.1 |
| DMEM | | 76.7 |
| + Antithrombin III | 25 | 94.0 |
| + APMSF | 40 | 74.0 |
| + Apurotinin | 2 | 73.6 |
| + Leupeptin | 0.5 | 65.5 |
| + AEBSF | 50 | 92.2 |
| + TLCK | 50 | 89.3 |

The results in Table 4 show that serum-free medium containing antithrombin III in a concentration of 25 μg/mL was highly effective in controlling cell death, resulting in virtually the same survival rate as that of medium containing 5% fetal bovine serum. A study of serum-free media containing the typical protease inhibitors APMSF, Apurotinin, Leupeptin, AEBSF, PMSF, and TLCK revealed that AEBSF and TLCK were effective in controlling cell death. The effects of antithrombin III in controlling cell death were thus attributed to serine protease inhibitor action.

The present invention relates to human and animal cell culture media containing antithrombin III, affording the following effects: 1) it can be used to control cell death, including the apoptosis of human and animal cells during serum-free culture; 2) it allows human and animal cells to be cultured at a high cell survival rate; and 3) it can be used to produce useful biological substances using human and animal cells, and it can also be used for biological analysis, and the like.

What is claimed is:

1. A method of suppressing cell death in a cell culture, comprising
    adding antithrombin III to a culture medium in an amount sufficient to suppress cell death; and
    culturing an animal cell in said culture medium.
2. The method of claim 1, wherein the animal cell is a human cell.
3. The method of claim 1, wherein the culture medium contains heparin.
4. The method of claim 1, wherein the concentration of the antithrombin III is 1 μg/ml or more.
5. The method of claim 1, wherein the concentration of the antithrombin III is from 25 to 50 μg/ml.
6. The method of claim 1, wherein the culture medium contains a serum.
7. A method for suppressing cell death in a cell culture, comprising culturing an animal cell in a culture medium containing purified antithrombin III in a concentration of 1 to 50 μg/ml.
8. The method of claim 7, wherein the purified antithrombin III is obtained from human serum, bovine serum, recombinant bacteria expressing antithrombin III, recombinant animal cells expressing antithrombin III or mixtures thereof.
9. The method of claim 8, wherein the purified antithrombin III is obtained from human serum.
10. The method of claim 8, wherein the purified antithrombin III is obtained from bovine serum.
11. The method of claim 8, wherein the purified antithrombin III is obtained from recombinant bacteria expressing antithrombin III.
12. The method of claim 8, wherein the purified antithrombin III is obtained from recombinant animal cells expressing antithrombin III.
13. The method of claim 7, wherein the animal cell is a human cell.
14. The method of claim 7, wherein the culture medium contains heparin.
15. The method of claim 14, wherein the antithrombin III is obtained from human serum, bovine serum, recombinant bacteria, recombinant animal cells expressing antithrombin III or mixtures thereof.
16. The method of claim 15, wherein the purified antithrombin III is obtained from human serum.
17. The method of claim 15, wherein the purified antithrombin III is obtained from bovine serum.
18. The method of claim 15, wherein the purified antithrombin III is obtained from recombinant bacteria expressing antithrombin III.
19. The method of claim 15, wherein the purified antithrombin III is obtained from recombinant animal cells expressing antithrombin III.
20. The method of claim 7, wherein the concentration of the antithrombin III is from 25 to 50 μg/ml.
21. The method of claim 7, wherein the culture medium contains a serum.

* * * * *